United States Patent [19]

Hester, Jr.

[11] B 3,996,230
[45] Dec. 7, 1976

[54] 1-PIPERAZINO-6-(2-PYRIDYL)-4H-S-TRIAZOLO[4,3-A][1,4]BENZODIAZEPINES

[75] Inventor: Jackson B. Hester, Jr., Galesburg, Mich.

[73] Assignee: The Upjohn Company, Kalamazoo, Mich.

[22] Filed: Mar. 28, 1975

[21] Appl. No.: 563,070

[44] Published under the second Trial Voluntary Protest Program on March 9, 1976 as document No. B 563,070.

[52] U.S. Cl. .................. 260/268 TR; 260/239.3 D; 260/296 T; 424/250
[51] Int. Cl.² ..................................... C07D 295/12
[58] Field of Search .............................. 260/268 TR

[56] References Cited
UNITED STATES PATENTS

| | | | |
|---|---|---|---|
| 3,503,957 | 3/1970 | Drukker et al. | 260/268 TR |
| 3,842,090 | 10/1974 | Gall et al. | 260/268 TR |
| 3,846,421 | 11/1974 | Meguro et al. | 260/268 TR |
| 3,870,714 | 3/1975 | Gagneux et al. | 260/268 TR |
| 3,878,205 | 7/1972 | Gagneux et al. | 260/268 TR |
| 3,894,025 | 7/1975 | Hester, Jr. | 260/268 TR |

*Primary Examiner*—Richard J. Gallagher
*Assistant Examiner*—Jose Tovar
*Attorney, Agent, or Firm*—Hans L. Berneis

[57] ABSTRACT

1-Piperazino-6-(2-pyridyl)-4H-s-triazolo[4,3-a][1,4]benzodiazepines of the formula II:

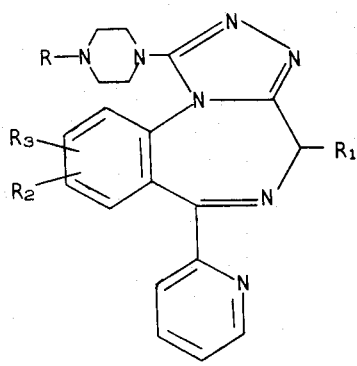

wherein R is hydrogen, alkyl of 1 to 3 carbon atoms, inclusive, or β-hydroxyethyl; wherein $R_1$ is hydrogen or alkyl defined as above; and wherein $R_2$ and $R_3$ are hydrogen, alkyl as defined above, fluoro, chloro, bromo, nitro or trifluoromethyl, are obtained by reacting a compound of the formula I:

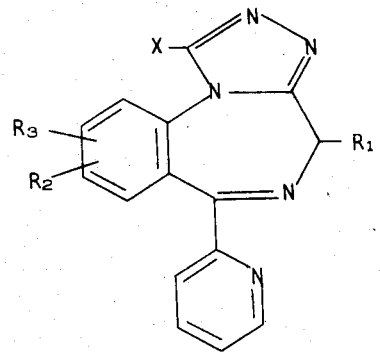

wherein $R_1$, $R_2$, and $R_3$ are defined as above and wherein X is chloro or bromo with a piperazine of the formula:

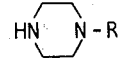

wherein R is defined as above.

The compounds of the formula II and their pharmacologically acceptable acid addition salts thereof, have tranquilizing, sedative and anti-depressant effects, and are useful for suppression of anxiety and depression in mammals and birds.

8 Claims, No Drawings

1-PIPERAZINO-6-(2-PYRIDYL)-4H-s-TRIAZOLO[4,3-a][1,4]BENZODIAZEPINES

BACKGROUND OF THE INVENTION

1. Field of the Invention

This invention is directed to a new class of organic compounds and is more particularly concerned with 1-piperazino-6-(2-pyridyl)-4H-s-triazolo[4,3-a][1,4]benzodiazepines (II) and a process of production therefor.

The novel compounds II and the process of production therefor can be illustratively represented as follows:

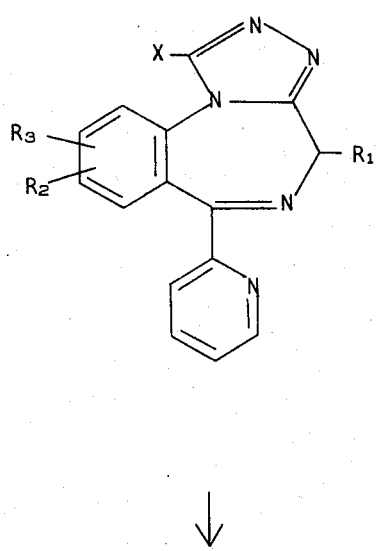

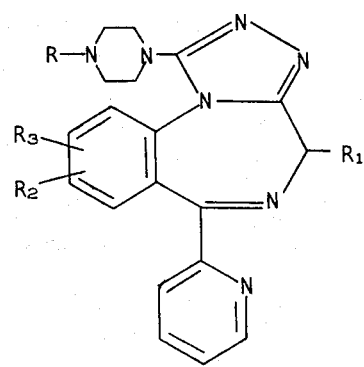

wherein R is hydrogen, alkyl of 1 to 3 carbon atoms, inclusive, or β-hydroxyethyl; wherein $R_1$ is hydrogen or alkyl defined as above; and wherein $R_2$ and $R_3$ are hydrogen, alkyl as defined above, fluoro, chloro, bromo, nitro, or trifluoromethyl, and wherein X is chloro or bromo.

The invention further comprises the pharmacologically acceptable acid addition salts of the compounds of formula II.

The more desirable products are of the formula IIA;

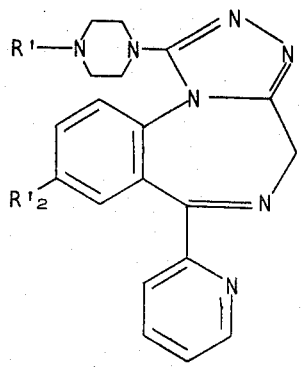

wherein R' is hydrogen, methyl, ethyl, or β-hydroxyethyl; $R'_2$ is hydrogen, fluoro, chloro, bromo, nitro, or trifluoromethyl, and the pharmacologically acceptable acid addition salts of the compounds of formula IIA.

The most desirable products are of the formula IIB:

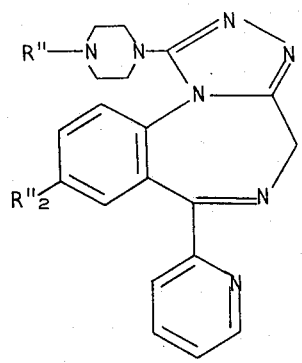

wherein R'' is methyl, ethyl, or β-hydroxyethyl; and wherein $R''_2$ is hydrogen, fluoro, chloro, or bromo, and the pharmacologically acceptable acid addition salts thereof.

The process of this application comprises: heating to 100° to 150° C. compound of formula I with an excess of the selected piperazine of the formula:

wherein R is defined as hereinabove, for a period of 6 to 24 hours, to obtain the corresponding compound of formula II.

DESCRIPTION OF THE PREFERRED EMBODIMENT

Lower alkyl groups of 1 to 3 carbon atoms, inclusive, are exemplified by methyl, ethyl, propyl, and isopropyl.

The novel compounds of the formula II including compounds IIA and IIB and the acid addition salts thereof, have sedative, tranquilizing and antidepressant effects in mammals and birds.

The acid addition salts of compounds of formula II, including IIA and IIB contemplated in this invention, are the hydrochlorides, hydrobromides, hydriodides, sulfates, phosphates, cyclohexanesulfamates, methanesulfonates, and the like, prepared by reacting a compound of formula II with an excess of the selected pharmacologically acceptable acid.

Sedative effects of the novel compounds II were shown by the following tests in mice:

Chimney test: [Med. Exp. 4, 145 (1961)]: The test determines the ability of mice to back up and out of a vertical glass cylinder within 30 seconds. At the effective dosage, 50% of the mice failed doing it.

Dish test: Mice in Petri dishes (10 cm. diameter, 5 cm. high, partially embedded in wood shavings), climb out in a very short time, when not treated. Mice remaining in the dish for more than 3 minutes indicates tranquilization. $ED_{50}$ equals the dose of test compound at which 50% of the mice remain in the dish.

Pedestal test: The untreated mouse leaves the pedestal in less than a minute to climb back to the floor of the standard mouse box. Tranquilized mice will stay on the pedestal for more than 1 minute.

Nicotine antagonism test: Mice in a group of 6 are injected with the test compound. Thirty minutes later the mice including control (untreated) mice are injected with nicotine salicylate (2 mg./kg.). The control mice show overstimulation, i.e., (1) running convulsions followed by (2) tonic extensor fits; followed by (3) death.

In addition the novel compounds potentiated the lethal effects of yohimbine, antagonized oxotremorine hypothermia and potentiated apomorphine gnawing, which are all tests known in the art to show antidepressant activity.

Thus, these compounds are useful for tranquilization, sedation, treating anxieties, and also useful as antidepressants in mammals and birds.

The pharmaceutical forms contemplated by this invention include pharmaceutical compositions suited for oral, parenteral, and rectal use, e.g., tablets, powder packets, cachets, dragees, capsules, solutions, suspensions, sterile injectable forms, suppositories, bougies, and the like. Suitable diluents or carriers such as carbohydrates (lactose), proteins, lipids, calcium phosphate, corn starch, stearic acid, methylcellulose and the like may be used as carriers or for coating purposes. Water or oil, e.g., coconut oil, sesame oil, safflower oil, cottonseed oil, peanut oil may be used for preparing solutions or suspensions of the active drug. Sweentening, coloring, and flavoring agents may be added.

For mammals and birds, food premixes with starch, oatmeal, dried fishmeat, fishmeal, flour and the like can be prepared.

As anti-anxiety agent and tranquilizer the compounds of formula II can be used in unit dosages of 0.05–10 mg./kg.; preferably in unit dosages of 0.1–5 mg./kg. in oral or injectable preparations as described above, the alleviate tension and anxiety in mammals, or birds, such as e.g., occurs when animals are in travel.

Other acid addition salts of the compounds of formula II can be made, such as the fluosilicic acid addition salts which are useful mothproofing compounds or the trichloroacetates useful las herbicides against Johnson grass, Bermuda grass, yellow foxtail and green foxtail, and quack grass.

The starting materials of formula I of this invention are prepared as shown in the preparations:

In carrying out the process of this invention, a selected 1-bromo- or 1-chloro-6-(2-pyridyl)-4H-s-triazolo[4,3-a][1,4]benzodiazepine (I), is heated in a considerable excess of the selected piperazine in which R is defined as herein above. The piperazine simultaneously serves as solvent and reactant. This mixture is heated preferably between 100° to 150° C. for a period of 6 to 24 hours. After the reaction is terminated the product is isolated and purified by conventional procedures e.g. extraction, evaporation of the extract, crystallization and chromatography.

The following preparations and examples are illustrative of the processes and products of the present invention, but are not to be construed as limiting.

PREPARATION 1

7-Bromo-5-(2-pyridyl)-2-hydrazino-3H-1,4-benzodiazepine

A stirred mixture of 7-bromo-1,3-dihydro-5-(2-pyridyl)-2H-1,4-benzodiazepine-2-thione (16.01 g., 0.048 mole) in methanol (400 ml.) is treated with hydrazine hydrate (7.51 g., 0.15 mole) and the flask equipped with nitrogen gas bubbling through the solution. The reaction is maintained at ambient temperature for 18 hours. The solid is collected by filtration, washed with methanol and dried in vacuo to give 13.57 g., of 7-bromo-5-(2-pyridyl)-2-hydrazino-3H-1,4-benzodiazepine of melting point 224°–225° C. (with foaming). A second crop is obtained by concentrating the filtrate and collecting the precipitate to give 0.79 g., of melting point 210°–212° C. (with foaming). The analytical sample is recrystallized from chloroform-methanol and has a melting point 224°–226° C. (with foaming).

Anal. calcd. for $C_{14}H_{12}BrN_5$: C, 50.93; H, 3.66; Br, 24.20; N, 21.21. Found: C, 50.77; H, 3.82; Br, 24.22; N, 21.29.

PREPARATION 2

8-Bromo-6-(2-pyridyl)-4H-s-triazolo-[4,3a][1,4]benzodiazepine

A stirred solution of 7-bromo-5-(2-pyridyl)-2-hydrazino-3H-1,4-benzodiazepine (3.30 g., 0.01 mole) and chloroform (80 ml.) is cooled in an ice bath, under nitrogen, and treated with triethyl orthoformate (7.41 g., 0.005 mole) and sulfuric acid (3.68 g.). The mixture is allowed to warm to ambient temperature and stir for 3 hours. The mixture is mixed with water, neutralized with sodium bicarbonate and the solution extracted with chloroform. The extract is washed with brine, dried over anhydrous sodium sulfate and concentrated in vacuo. The residue is chromatographed on silica gel using 5% methanol-95% chloroform. The product thus obtained is crystallized from ethyl acetate and recrystallized from methylene chloride-ethyl acetate to give 1.75 g. of 8-bromo-6-(2-pyridyl)-4H-s-triazolo[4,3-a][1,4]benzodiazepine of melting point 252°–255° C. The analytical sample has a melting point 252°–255° C.

Anal. calcd. for $C_{15}H_{10}BrN_5$: C, 52.96; H, 2.96; Br, 23.49; N, 20.59. Found; C, 52.83; H, 3.13; Br, 23.50; N, 20.98.

PREPARATION 3

1,8-Dibromo-6-(2-pyridyl)-4H-s-triazolo[4,3-a][1,4]benzodiazepine

A stirred mixture of 8-bromo-6-(2-pyridyl)-4H-s-triazolo[4,3-a][1,4]benzodiazepine (4.81 g., 0.0142 mole), N-bromosuccinimide (2.77 g., 0.0156 mole) and dry benzene (350 ml.), under nitrogen, is warmed in an oil bath from 51° to 83° C. during 45 minutes and refluxed gently for 3 hours, 20 minutes. The mixture is concentrated and the residual solid is suspended in a mixture of saturated aqueous sodium bicarbonate and chloroform and stirred for 45 minutes. The mixture is filtered and the solid is washed with water and chloroform, dried and crystallized from chloroform-methanol to give 1.12 g. and 0.368 g. of the brominated product. The above filtrate is extracted with chloroform. The extract is washed with brine, dried (anhydrous sodium sulfate) and concentrated. Crystallization of the residue from chloroform-methanol gives 1.27 g. of additional product. The mother liquors from these crystallizations are combined and chromatographed on silica gel (150 g.) with 98% chloroform-2% methanol to give 0.256 g. of 1,8-dibromo-6-(2-pyridyl)-4H-s-triazolo[4,3-a][1,4]benzodiazepine. Further elution of the column gives recovered starting material which is crystallized from methanol-ethyl acetate to give 0.352 g. of melting point 236.5°–238.5° C. The analytical sample of 1,8-dibromo-6-(2-pyridyl)-4H-s-triazolo[4,3-a][1,4]benzodiazepine crystallizes from methylene chloride-methanolethyl acetate. It darkens at about 250° C. but does not melt.

Anal. calcd. for $C_{15}H_9Br_2N_5$: C, 42.99; H, 2.16; Br, 38.14; N, 16.71. Found: C, 42.74; H, 2.47; Br, 38.48; N, 16.44.

Following the procedure of Preparation 1, but substituting other known representative 1,3-dihydro-2H-1,4-benzodiazepine-2-thiones such as:

1,3-dihydro-3-methyl-5-(2-pyridyl)-2H-1,4-benzodiazepine-2-thione;
1,3-dihydro-7-fluoro-5-(2-pyridyl)-2H-1,4-benzodiazepine-2-thione;
7-chloro-1,3-dihydro-5-(2-pyridyl)-2H-1,4-benzodiazepine-2-thione;
1,3-dihydro-5-(2-pyridyl)-7-(trifluoromethyl)-2H-1,4-benzodiazepine-2-thione;
3-ethyl-1,3-dihydro-5-(2-pyridyl)-7-(trifluoromethyl)-2H-1,4-benzodiazepine-2-thione;
1,3-dihydro-3-propyl-5-(2-pyridyl)-7-(trifluoromethyl)-2H-1,4-benzodiazepine-2-thione;
1,3-dihydro-5-(2-pyridyl)-7-nitro-2H-1,4-benzodiazepine-2-thione;
7-bromo-1,3-dihydro-5-(2-pyridyl)-8-nitro-2H-1,4-benzodiazepine-2-thione;
7-chloro-1,3-dihydro-5-(2-pyridyl)-9-(trifluoromethyl)-2H-1,4-benzodiazepine-2-thione;
7-fluoro-1,3-dihydro-3-propyl-5-(2-pyridyl)-8-(trifluoromethyl)-2H-1,4-benzodiazepine-2-thione;
1,3-dihydro-5-(2-pyridyl)-2H-1,4-benzodiazepine-2-thione; 1,3-dihydro-7-bromo-9-nitro-5-(2-pyridyl)-2H-1,4-benzodiazepine-2-thione;
7-chloro-9-methyl-1,3-dihydro-5-(2-pyridyl)-2H-1,4-benzodiazepine-2-thione;
1,3-dihydro-7-nitro-8-ethyl-5-(2-pyridyl)-2H-1,4-benzodiazepine-2-thione;
7-bromo-1,3-dihydro-9-methyl-5-(2-pyridyl)-2H-1,4-benzodiazepine-2-thione;
7-bromo-1,3-dihydro-3-methyl-5-(2-pyridyl)-2H-1,4-benzodiazepine-2-thione;
7-chloro-1,3-dihydro-3-ethyl-5-(2-pyridyl)-2H-1,4-benzodiazepine-2-thione;
7-bromo-8-fluoro-1,3-dihydro-5-(2-pyridyl)-2H-1,4-benzodiazepine-2-thione;
7-chloro-1,3-dihydro-8-bromo-5-(2-pyridyl)-2H-1,4-benzodiazepine-2-thione;

or the like, there are obtained the corresponding 2-hydrazino compounds such as:

2-hydrazino-3-methyl-5-(2-pyridyl)-3H-1,4-benzodiazepine;
7-fluoro-2-hydrazino-5-(2-pyridyl)-3H-1,4-benzodiazepine;
7-chloro-2-hydrazino-5-(2-pyridyl)-3H-1,4-benzodiazepine;
7-(trifluoromethyl)-2-hydrazino-5-(2-pyridyl)-3H-1,4-benzodiazepine;
7-(trifluoromethyl)-2-hydrazino-3-ethyl-5-(2-pyridyl)-3H-1,4-benzodiazepine;
7-(trifluoromethyl)-2-hydrazino-3-propyl-5-(2-pyridyl)-3H-1,4-benzodiazepine;
7-nitro-2-hydrazino-5-(2-pyridyl)-3H-1,4-benzodiazepine;
7-bromo-8-nitro-2-hydrazino-5-(2-pyridyl)-3H-1,4-benzodiazepine;
7-chloro-9-(trifluoromethyl)-2-hydrazino-5-(2-pyridyl)-3H-1,4-benzodiazepine;
7-fluoro-2-hydrazino-3-propyl-5-(2-pyridyl)-8-(trifluoromethyl)-3H-1,4-benzodiazepine;
2-hydrazino-5-(2-pyridyl)-3H-1,4-benzodiazepine;
7-bromo-9-nitro-2-hydrazino-5-(2-pyridyl)-3H-1,4-benzodiazepine;
7-chloro-9-methyl-2-hydrazino-5-(2-pyridyl)-3H-1,4-benzodiazepine;
7-nitro-8-ethyl-2-hydrazino-5-(2-pyridyl)-3H-1,4-benzodiazepine;
7-bromo-9-methyl-2-hydrazino-5-(2-pyridyl)-3H-1,4-benzodiazepine;
7-bromo-3-methyl-2-hydrazino-5-(2-pyridyl)-3H-1,4-benzodiazepine;
7-chloro-3-ethyl-2-hydrazino-5-(2-pyridyl)-3H-1,4-benzodiazepine;
7-bromo-8-fluoro-2-hydrazino-5-(2-pyridyl)-3H-1,4-benzodiazepine;
7-chloro-8-bromo-2-hydrazino-5-(2-pyridyl)-3H-1,4-benzodiazepine;

or the like.

When the above compounds are treated with triethyl orthoformate as shown in Preparation 2 and the thus obtained products are brominated e.g. with N-bromosuccinimide as shown in Preparation 3, the following compounds are obtained:

1-bromo-4-methyl-6-(2-pyridyl)-4H-s-triazolo[4,3-a][1,4]-benzodiazepine;
1-bromo-8-fluoro-6-(2-pyridyl)-4H-s-triazolo[4,3-a][1,4]benzodiazepine;
1-bromo-8-chloro-6-(2-pyridyl)-4H-s-triazolo[4,3-a][1,4]benzodiazepine,
1-bromo-8-(trifluoromethyl)-6-(2-pyridyl)-4H-s-triazolo[4,3-a][1,4]benzodiazepine;
1-bromo-8-(trifluoromethyl)-4-ethyl-6-(2-pyridyl)-4H-s-triazolo[4,3-a][1,4]benzodiazepine;
1-bromo-8-(trifluoromethyl)-4-propyl-6-(2-pyridyl)-4H-s-triazolo[4,3-a][1,4]benzodiazepine;
1-bromo-8-nitro-6-(2-pyridyl)-4H-s-triazolo[4,3-a][1,4]benzodiazepine;
1,8-dibromo-9-nitro-6-(2-pyridyl)-4H-s-triazolo[4,3-a][1,4]benzodiazepine;
1-bromo-8-chloro-9-(trifluoromethyl)-6-(2-pyridyl)-4H-s-triazolo[4,3-a][1,4]benzodiazepine;
1-bromo-8-fluoro-4-propyl-6-(2-pyridyl)-9-(trifluoromethyl)-4H-s-triazolo[4,3-a][1,4]benzodiazepine;
1-bromo-6-(2-pyridyl)-4H-s-triazolo[4,3-a][1,4]benzodiazepine;

1,8-dibromo-10-nitro-6-(2-pyridyl)-4H-s-triazolo[4,3-a][1,4]benzodiazepine;
1-bromo-8-chloro-10-methyl-6-(2-pyridyl)-4H-s-triazolo[4,3-a][1,4]benzodiazepine;
1-bromo-8-nitro-9-ethyl-6-(2-pyridyl)-4H-s-triazolo[4,3-a][1,4]benzodiazepine;
1,8-dibromo-10-methyl-6-(2-pyridyl)-4H-s-triazolo[4,3-a][1,4]benzodiazepine;
1,8-dibromo-4-methyl-6-(2-pyridyl)-4H-s-triazolo[4,3-a][1,4]benzodiazepine;
1-bromo-8-chloro-4-ethyl-6-(2-pyridyl)-4H-s-triazolo[4,3-a][1,4]benzodiazepine;
1,8-dibromo-9-fluoro-6-(2-pyridyl)-4H-s-triazolo[4,3-a][1,4]benzodiazepine;
1,9-dibromo-8-chloro-6-(2-pyridyl)-4H-s-triazolo[4,3-a][1,4]benzodiazepine;

and the like.

If N-chlorosuccinimide, N-chloroacetamide or other chlorinating agents are used instead of N-bromosuccinimide the corresponding 1-chloro analogues of the above compounds are obtained.

EXAMPLE 1

8-Bromo-1-(4-methylpiperazino)-6-(2-pyridyl)-4H-s-triazolo[4,3-a][1,4]benzodiazepine A stirred mixture of 1,8-dibromo-6-(2-pyridyl)-4H-s-triazolo[4,3-a][1,4]benzodiazepine (2.19 g.) and 1-methylpiperazine (10 ml.) is kept under nitrogen at 125°–130° C. for 15.5 hours and at 135°–145° C. for 24 hours. It is then cooled, mixed with cold water, treated with a little sodium bicarbonate and extracted with chloroform. The extract is washed with brine, dried over anhydrous sodium sulfate and concentrated. The residue is treated successively with xylene and toluene with concentration after each addition and the resulting material is chromatographed on silica gel (150 g.) with mixtures of chloroform and methanol containing 5–10% methanol. The product thus obtained is crystallized from methanol-ethyl acetate to give 8-bromo-1-(4-methylpiperazino)-6-(2-pyridyl)-4H-s-triazolo[4,3-a][1,4]benzodiazepine in 4 crops as follows: 0.799 g., melting point 250.5°–253.5° dec; 0.062 g., melting point 248.5–249.5° dec; 0.344 g., melting point 250°–252° dec., and 0.206 g., melting point 245.5°–247.5° dec. The analytical sample has a melting point of 252°–253° dec.

Anal. calcd. for $C_{20}H_{20}BrN_7$: C, 54.80; H, 4.60; Br, 18.23; N, 22.37. Found: C, 54.58; H, 4.57; Br, 18.19; N, 22.52.

EXAMPLE 2

8-Chloro-1-(4-methylpiperazino)-6-(2-pyridyl)-4H-s-triazolo[4,3-a][1,4]benzodiazepine In the manner given in Example 1, 8-chloro-1-bromo-6-(2-pyridyl)-4H-s-triazolo[4,3-a][1,4]benzodiazepine is heated with 1-methylpiperazine to give 8-chloro-1-(4-methylpiperazino)-6-(2-pyridyl)-4H-s-triazolo[4,3-a][1,4]benzodiazepine.

EXAMPLE 3

8-Bromo-1-[4-(β-hydroxyethyl)piperazino]-6-(2-pyridyl)-4H-s-triazolo[4,3-a][1,4]benzodiazepine In a manner given in Example 1, 1,8-dibromo-6-(2-pyridyl)-4H-s-triazolo[4,3-a][1,4]benzodiazepine is heated with excess 1-(β-hydroxyethyl)piperazine to give 8-bromo-1-[4-(β-hydroxyethyl)piperazino]-6-(2-pyridyl)-4H-s-triazolo[4,3-a][1,4]benzodiazepine.

EXAMPLE 4

4-Methyl-1-piperazino-6-(2-pyridyl)-4H-s-triazolo[4,3-a][1,4]benzodiazepine

In the manner given in Example 1, 1-bromo-4-methyl-6-(2-pyridyl)-4H-s-triazolo[4,3-a][1,4]benzodiazepine is heated with piperazine to give 4-methyl-1-(piperazino)-6-(2-pyridyl)-4H-s-triazolo[4,3-a][1,4]benzodiazepine.

EXAMPLE 5

8-Chloro-1-(4-ethylpiperazino)-6-(2-pyridyl)-4H-s-triazolo[4,3-a][1,4]benzodiazepine In the manner given in Example 1, 1-bromo-8-chloro-6-(2-pyridyl)-4H-s-triazolo[4,3-a][1,4]benzodiazepine is heated with excess of 1-ethylpiperazine to give 8-chloro-1-(4-ethylpiperazino)-6-(2-pyridyl)-4H-s-triazolo[4,3-a][1,4]benzodiazepine.

EXAMPLE 6

8-(Trifluoromethyl)-1-(4-methylpiperazino)-6-(2-pyridyl)-4H-s-triazolo[4,3-a][1,4]benzodiazepine In the manner given in Example 1, 8-(trifluoromethyl)-1-bromo-6-(2-pyridyl)-4H-s-triazolo[4,3-a][1,4]benzodiazepine is heated with 1-methylpiperazine to give 8-(trifluoromethyl)-1-(4-methylpiperazino)-6-(2-pyridyl)-4H-s-triazolo[4,3-a][1,4]benzodiazepine.

EXAMPLE 7

8-(Trifluoromethyl)-4-ethyl-1-piperazino-6-(2-pyridyl)-4H-s-triazolo[4,3-a][1,4]benzodiazepine In the manner given in Example 1, 1-bromo-8-(trifluoromethyl)-4-ethyl-6-(2-pyridyl)-4H-s-triazolo[4,3-a][1,4]benzodiazepine is heated with excess of piperazine to give 8-(trifluoromethyl)-4-ethyl-1-piperazino-6-(2-pyridyl)-4H-s-triazolo[4,3-a][1,4]benzodiazepine.

EXAMPLE 8

8-(Trifluoromethyl)-1-(4-isopropylpiperazino)-6-(2-pyridyl)-4H-s-triazolo[4,3-a][1,4]benzodiazepine In the manner given in Example 1, 8-(trifluoromethyl)-1-bromo-6-(2-pyridyl)-4H-s-triazolo[4,3-a][1,4]benzodiazepine is heated with 1-isopropylpiperazine to give 8-(trifluoromethyl)-1-(4-isopropylpiperazino)-6-(2-pyridyl)-4H-s-triazolo[4,3-a][1,4]benzodiazepine.

EXAMPLE 9

8-Nitro-1-[4-(β-hydroxyethyl)piperazino]-6-(2-pyridyl)-4H-s-triazolo[4,3-a][1,4]benzodiazepine In the manner given in Example 1, 1-bromo-8-nitro-6-(2-pyridyl)-4H-s-triazolo[4,3-a][1,4]benzodiazepine is heated with excess 1-(β-hydroxyethyl)piperazine to give 8-nitro-1-[4-(β-hydroxyethyl)piperazino]-6-(2-pyridyl)-4H-s-triazolo[4,3-a][1,4]benzodiazepine.

EXAMPLE 10

8-Bromo-9-nitro-1-(4-methylpiperazino)-6-(2-pyridyl)-4H-s-triazolo[4,3-a][1,4]benzodiazepine In the manner given in Example 1, 1,8-dibromo-9-nitro-6-(2-pyridyl)-4H-s-triazolo[4,3-a][1,4]benzodiazepine is heated with 1-methylpiperazine to give 8-bromo-9-nitro-1-(4-methylpiperazino)-6-(2-pyridyl)-4H-s-triazolo[4,3-a][1,4]benzodiazepine.

EXAMPLE 11

8-Chloro-9-(trifluoromethyl)-1-piperazino-6-(2-pyridyl)-4H-s-triazolo[4,3-a][1,4]benzodiazepine In the manner given in Example 1, 1-bromo-8-chloro-9-(trifluoromethyl)-6-(2-pyridyl)-4H-s-triazolo[4,3-a][1,4]benzodiazepine is heated with excess of piperazine to give 8-chloro-9-(trifluoromethyl)-1-piperazino-6-(2-pyridyl)-4H-s-triazolo[4,3-a][1,4]benzodiazepine.

EXAMPLE 12

8-Fluoro-4-propyl-1-(4-ethylpiperazino)-6-(2-pyridyl)-4H-s-triazolo[4,3-a][1,4]benzodiazepine In the manner given in Example 1, 1-bromo-8-fluoro-4-propyl-6-(2-pyridyl)-4H-s-triazolo[4,3-a][1,4]benzodiazepine is heated with 1-ethylpiperazine to give 8-fluoro-4-propyl-1-(4-ethylpiperazino)-6-(2-pyridyl)-4H-s-triazolo[4,3-a][1,4]benzodiazepine.

EXAMPLE 13

1-(4-Methylpiperazino)-6-(2-pyridyl)-4H-s-triazolo[4,3-a][1,4]benzodiazepine

In the manner given in Example 1, 1-bromo-6-(2-pyridyl)-4H-s-triazolo[4,3-a][1,4]benzodiazepine is heated with excess 1-methylpiperazine to give 1-(4-methyl-piperazino)-6-(2-pyridyl)-4H-s-triazolo[4,3-a][1,4]benzodiazepine.

EXAMPLE 14

8-Bromo-10-nitro-1-(4-ethylpiperazino)-6-(2-pyridyl)-4H-s-triazolo[4,3-a][1,4]benzodiazepine In the manner given in Example 1, 1,8-dibromo-10-nitro-6-(2-pyridyl)-4H-s-triazolo[4,3-a][1,4]benzodiazepine is heated with 1-ethylpiperazine to give 8-bromo-10-nitro-1-(4-ethylpiperazino)-6-(2-pyridyl)-4H-s-triazolo[4,3-a][1,4]benzodiazepine.

EXAMPLE 15

1-[4-(β-Hydroxyethyl)piperazino]-6-(2-pyridyl)-4H-s-triazolo[4,3-a][1,4]benzodiazepine In the manner given in Example 1, 1-bromo-6-(2-pyridyl)-4H-s-triazolo[4,3-a][1,4]benzodiazepine is heated with excess 1-(β-hydroxyethyl)piperazine to give 1-[4-(β-hydroxyethyl)piperazino]-6-(2-pyridyl)-4H-s-triazolo[4,3-a][1,4]benzodiazepine.

EXAMPLE 16

8-Chloro-10-methyl-1-(4-methylpiperazino)-6-(2-pyridyl)-4H-s-triazolo[4,3-a][1,4]benzodiazepine In the manner given in Example 1, 1-bromo-8-chloro-10-methyl-6-(2-pyridyl)-4H-s-triazolo[4,3-a][1,4]benzodiazepine is heated with 1-methylpiperazine to give 8-chloro-10-methyl-1-(4-methylpiperazino)-6-(2-pyridyl)-4H-s-triazolo[4,3-a][1,4]benzodiazepine.

EXAMPLE 17

9-Ethyl-7-nitro-1-[4-(β-hydroxyethyl)piperazino]-6-(2-pyridyl)-4H-s-triazolo[4,3-a][1,4]benzodiazepine In the manner given in Example 1, 1-bromo-9-ethyl-7-nitro-6-(2-pyridyl)-4H-s-triazolo[4,3-a][1,4]benzodiazepine is heated with excess 1-(β-hydroxyethyl)piperazine to give 1-(β-hydroxyethyl)piperazino-6-(2-pyridyl)-4H-s-triazolo[4,3-a][1,4]benzodiazepine.

EXAMPLE 18

8-Bromo-10-methyl-1-(4-methylpiperazino)-6-(2-pyridyl)-4H-s-triazolo[4,3-a][1,4]benzodiazepine In the manner given in Example 1, 1,8-dibromo-10-methyl-6-(2-pyridyl)-4H-s-triazolo[4,3-a][1,4]benzodiazepine is heated with 1-methylpiperazine to give 8-bromo-10-methyl-1-(4-methylpiperazino)-6-(2-pyridyl)-4H-s-triazolo[4,3-a][1,4]benzodiazepine.

EXAMPLE 19

8-Bromo-4-methyl-1-[4-(β-hydroxyethyl)piperazino]-6-(2-pyridyl)-4H-s-triazolo[4,3-a][1,4]benzodiazepine In the manner given in Example 1, 1,8-dibromo-4-methyl-6-(2-pyridyl)-4H-s-triazolo[4,3-a][1,4]benzodiazepine is heated with excess of 1-(β-hydroxyethyl)piperazine to give 8-bromo-4-methyl-1-[4-(β-hydroxyethyl)piperazino]-6-(2-pyridyl)-4H-s-triazolo[4,3-a][1,4]benzodiazepine.

EXAMPLE 20

8-Chloro-4-ethyl-1-piperazino-6-(2-pyridyl)-4H-s-triazolo[4,3-a][1,4]benzodiazepine In the manner given in Example 1, 1,8-dichloro-4-ethyl-6-(2-pyridyl)-4H-s-triazolo[4,3-a][1,4]benzodiazepine is heated with piperazine to give 8-chloro-4-ethyl-1-piperazino-6-(2-pyridyl)-4H-s-triazolo[4,3-a][1,4]benzodiazepine.

EXAMPLE 21

8-Bromo-9-fluoro-1-(4-propylpiperazino)-6-(2-pyridyl)-4H-s-triazolo[4,3-a][1,4]benzodiazepine In the manner given in Example 1, 1,8-dibromo-9-fluoro-6-(2-pyridyl)-4H-s-triazolo[4,3-a][1,4]benzodiazepine is heated with excess 1-propylpiperazine to give 8-bromo-9-fluoro-1-(4-propylpiperazino)-6-(2-pyridyl)-4H-s-triazolo[4,3-a][1,4]benzodiazepine.

EXAMPLE 22

9-Bromo-8-chloro-1-(4-methylpiperazino)-6-(2-pyridyl)-4H-s-triazolo[4,3-a][1,4]benzodiazepine In the manner given in Example 1, 1,9-dibromo-8-chloro-6-(2-pyridyl)-4H-s-triazolo[4,3-a][1,4]benzodiazepine is heated with 1-methylpiperazine to give 9-bromo-8-chloro-1-(4-methylpiperazino)-6-(2-pyridyl)-4H-s-triazolo[4,3-a][1,4]benzodiazepine.

EXAMPLE 23

8-Chloro-1-[4-(β-hydroxyethyl)piperazino]-6-(2-pyridyl)-4H-s-triazolo[4,3-a][1,4]benzodiazepine In the manner given in Example 1, 1-bromo-8-chloro-6-(2-pyridyl)-4H-s-triazolo[4,3-a][1,4]benzodiazepine is heated with excess 1-(β-hydroxyethyl)piperazine to give 8-chloro-1-[4-(β-hydroxyethyl)piperazino]-6-(2-pyridyl)-4H-s-triazolo[4,3-a][1,4]benzodiazepine.

EXAMPLE 24

8-Bromo-1-piperazino-6-(2-pyridyl)-4H-s-triazolo[4,3-a][1,4]benzodiazepine

In the manner given in Example 1, 1,8-dibromo-6-(2-pyridyl)-4H-s-triazolo[4,3-a][1,4]benzodiazepine is heated with piperazine to give 8-bromo-1-piperazino-6-(2-pyridyl)-4H-s-triazolo[4,3-a][1,4]benzodiazepine.

EXAMPLE 25

8-Fluoro-1-[4-(β-hydroxyethyl)piperazino]-6-(2-pyridyl)-4H-s-triazolo[4,3-a][1,4]benzodiazepine In the manner given in Example 1, 1-bromo-8-fluoro-6-(2-pyridyl)-4H-s-triazolo[4,3-a][1,4]benzodiazepine is heated with excess 1-(β-hydroxyethyl)piperazine to give 8-fluoro-1-[4-(β-hydroxyethyl)piperazino]-6-(2-pyridyl)-4H-s-triazolo[4,3-a][1,4]benzodiazepine.

In the same manner given in the prior examples other compounds of formula II can be made such as:

4,7,9-trimethyl-1-(4-methylpiperazino)-6-(2-pyridyl)-4H-s-triazolo[4,3-a][1,4]benzodiazepine;
4,8-dimethyl-1-(4-ethylpiperazino)-6-(2-pyridyl)-4H-s-triazolo[4,3-a][1,4]benzodiazepine;
8-isopropyl-1-(4-propylpiperazino)-6-(2-pyridyl)-4H-s-triazolo[4,3-a][1,4]benzodiazepine;
9,10-dichloro-1-(4-methylpiperazino)-6-(2-pyridyl)-4H-s-triazolo[4,3-a][1,4]benzodiazepine;
7,9-dinitro-1-piperazino-6-(2-pyridyl)-4H-s-triazolo[4,3-a][1,4]benzodiazepine;
8,9-dichloro-1-(4-methylpiperazino)-6-(2-pyridyl)-4H-s-triazolo[4,3-a][1,4]benzodiazepine;
8,10-difluoro-1-(4-methylpiperazino)-6-(2-pyridyl)-4H-s-triazolo[4,3-a][1,4]benzodiazepine;
10-fluoro-1-(4-methylpiperazino)-6-(2-pyridyl)-4H-s-triazolo[4,3-a][1,4]benzodiazepine;
7,10-bis(trifluoromethyl)-1-(4-methylpiperazino)-6-(2-pyridyl)-4H-s-triazolo[4,3-a][1,4]benzodiazepine;
8-bromo-9-(trifluoromethyl)-1-(4-ethylpiperazino)-6-(2-pyridyl)-4H-s-triazolo[4,3-a][1,4]benzodiazepine;
8-nitro-10-chloro-1-[4-(β-hydroxyethyl)piperazino]-6-(2-pyridyl)-4H-s-triazolo[4,3-a][1,4]benzodiazepine;
7-nitro-8-bromo-1-[4-(β-hydroxyethyl)piperazino]-6-(2-pyridyl)-4H-s-triazolo[4,3-a][1,4]benzodiazepine;
8-bromo-9-nitro-1-[4-(β-hydroxyethyl)piperazino]-6-(2-pyridyl)-4H-s-triazolo[4,3-a][1,4]benzodiazepine;

and the like.

Treating the compounds of formula II with pharmacologically acceptable acids such as hydrochloric, hydrobromic, phosphoric, sulfuric, acetic, propionic, toluenesulfonic, methanesulfonic, tartaric, citric, lactic, malic, maleic, and cyclohexanesulfamic acids produces the pharmacologically acceptable salts of these compounds of formula II which can be used like the free base compounds of formula II. Salt formation is achieved in conventional manner by reacting the compounds of formula II with excess of a selected acid in a suitable medium e.g. water, a lower alkanol, ether, or acetone and recovering the salt by evaporating the solvent, preferably in vacuo.

I claim:
1. A compound of the formula II:

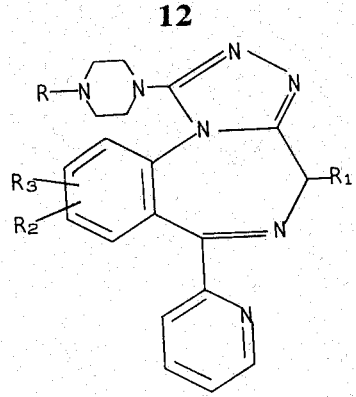

wherein R is hydrogen, alkyl of 1 to 3 carbon atoms, inclusive, or β-hydroxyethyl; wherein $R_1$ is hydrogen or alkyl defined as above; and wherein $R_2$ and $R_3$ are hydrogen, alkyl as definend above, fluoro, chloro, bromo, nitro, or trifluoromethyl, or the pharmacologically acceptable acid addition salts thereof.

2. A compound according to claim 1 having the formula IIA:

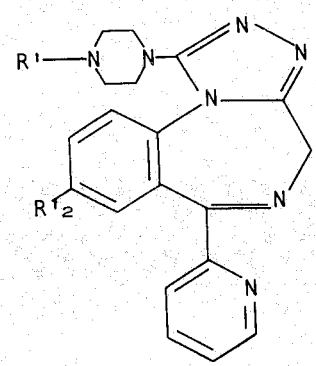

wherein R' is hydrogen, alkyl of 1 or 2 carbon atoms, inclusive, and β-hydroxyethyl; $R'_2$ is hydrogen, fluoro, chloro, bromo, nitro, or trifluoromethyl, or the pharmacologically acceptable acid addition salt of the compounds of formula IIA.

3. A compound according to claim 1 having the formula IIB:

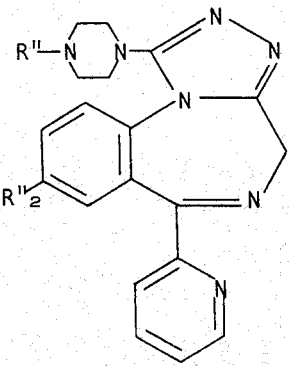

wherein R'' is methyl, ethyl, or β-hydroxyethyl, wherein R'' is hydrogen, fluoro, chloro, or bromo, or the pharmacologically acceptable acid addition salts thereof.

4. A compound according to claim 3, wherein R'' is methyl, $R''_2$ is bromo and the compound is therefore 8-bromo-1-(4-methylpiperazino)-6-(2-pyridyl)-4H-s-triazolo[4,3-a][1,4]benzodiazepine.

5. A compound according to claim 3, wherein R'' is β-hydroxyethyl, R''$_2$ is bromo, and the compound is therefore 8-bromo-1-[4-(β-hydroxyethyl)piperazino]-6-phenyl-4H-s-triazolo[4,3-a][1,4]benzodiazepine.

6. A compound according to claim 3, wherein R'' is methyl, R''$_2$ is chloro, and the compound is therefore 8-chloro-1-(4-methylpiperazino)-6-(2-pyridyl)-4H-s-triazolo[4,3-a][1,4]benzodiazepine.

7. A compound according to claim 3, wherein R'' is methyl, R''$_2$ is hydrogen, and the compound is therefore 1-(4-methylpiperazino)-6-(2-pyridyl)-4H-s-triazolo[4,3-a][1,4]benzodiazepine.

8. A compound according to claim 2, wherein R' is hydrogen, R'$_2$ is bromo, and the compound is therfore 8-bromo-1-piperazino-6-(2-pyridyl)-4H-s-triazolo[4,3-a][1,4]benzodiazepine.

* * * * *